US006299637B1

(12) United States Patent
Shaolian et al.

(10) Patent No.: US 6,299,637 B1
(45) Date of Patent: Oct. 9, 2001

(54) TRANSLUMINALLY IMPLANTABLE VENOUS VALVE

(76) Inventors: Samuel M. Shaolian, 2315 Arbutus St., Newport Beach, CA (US) 92660; Gerard von Hoffmann, 3 Via Presea, Trabuco Canyon, CA (US) 92679

( * ) Notice: Subject to any disclaimer, the term of this patent is extended or adjusted under 35 U.S.C. 154(b) by 0 days.

(21) Appl. No.: 09/378,386

(22) Filed: Aug. 20, 1999

(51) Int. Cl.⁷ .................................................. A61F 2/06
(52) U.S. Cl. .......................................... 623/1.24
(58) Field of Search .................... 623/1.24, 1.26, 623/2.1, 2.12, 2.14, 2.13, 1.25

(56) References Cited

U.S. PATENT DOCUMENTS

| | | |
|---|---|---|
| 4,904,254 | 2/1990 | Lane . |
| 4,994,077 * | 2/1991 | Dobben ............................. 623/2.1 |
| 5,147,389 | 9/1992 | Lane . |
| 5,358,518 * | 10/1994 | Camilli ............................. 623/2.1 |
| 5,370,685 | 12/1994 | Stevens . |
| 5,411,552 | 5/1995 | Andersen et al. . |
| 5,500,014 | 3/1996 | Quijano et al. . |
| 5,554,185 | 9/1996 | Block et al. . |
| 5,607,465 | 3/1997 | Camilli . |
| 5,609,598 | 3/1997 | Laufer et al. . |
| 5,824,061 | 10/1998 | Quijano et al. . |
| 5,824,071 | 10/1998 | Nelson et al. . |
| 5,830,222 | 11/1998 | Makower . |
| 5,851,232 | 12/1998 | Lois . |
| 5,855,601 | 1/1999 | Bessler et al. . |
| 5,951,502 | 9/1999 | Peeler et al. . |
| 5,957,949 | 9/1999 | Leohardt et al. . |

FOREIGN PATENT DOCUMENTS 0 856 300 A1    8/1998   (EP) .

OTHER PUBLICATIONS

Diameter–reflux relationship in perforating veins of patients with varicose veins, Joao Luis Sandri, MD, Fanilda S. Barros, MD, Sandra Pontes, MD, Clausio Jacques, MD, Sergio X. Salles–Cunha, Ph.D., Journal of Vascular Surgery, Nov. 1999, vol. 30, No. 5.

A multicenter, phase I evaluation of cryopreserved venous value allografts for the treatment of chronic deep venous insufficiency, Michael C. Dalsing, MD, Seshadri Raju, MD, Thomas W. Wakefield, MD, Syde Taheri, MD, Journal of Vascular Surgery, Nov. 1999, vol. 30, No. 5.

Lessons from the past guide the future: Is history truly circular?, Thomas F. O'Donnell Jr, MD, FACS, Journal of Vascular Surgery, Nov. 1999, vol. 30, No. 5.

The effect of graded compression elastic stockings on the lower leg venous system during daily activity, Chad L. Buhs, MD, Philip J. Bendick, PhD, John L. Glover, MD, Journal of Vascular Surgery, Nov. 1999, vol. 30, No. 5.

Deep venous thrombosis after precutaneous insertion of vena caval filters, John Blebea, MD, Ryan Wilson, RVT, Peter Waybill, MD, Marsha M. Neumyer, PVT, Judy S. Blebea, MD, Karla M. Anderson, MD, Robert G. Atnip, MD Journal of Vascular Surgery, Nov. 1999, vol. 30, No. 5.

(List continued on next page.)

*Primary Examiner*—David H. Willse
*Assistant Examiner*—Alvin Stewart
(74) *Attorney, Agent, or Firm*—Knobbe, Martens, Olson & Bear, LLP

(57) ABSTRACT

Disclosed is a self-expandable prosthetic venous valve, such as for implantation in the deep veins of the leg. The valve is mounted in a support structure, such as a self-expandable tubular wire cage. Deployment catheters and methods are also disclosed.

18 Claims, 4 Drawing Sheets

OTHER PUBLICATIONS

Sensory Impairment: A feature of chronic venous insufficiency, Frank T. Padberg Jr, MD, Allen H. Maniker, MD, Gwendolyn Carmel, RVT, Peter J. Pappas, MD, Michael B. Silva Jr, MD, Robert W. Hobson II, MD, Journal of Vascular Surgery, Nov. 1999, vol. 30, No. 5.

Experimental prosthetic vein valve, Slde A. Taheri, MD, Thomas Wormer, MD, Louis Lazar, MD, Julia Cullen, MD, Helene Burgio, R.N., *International Angiology*, vol. 8, No. 1, Jan.–Mar. 1989.

Distribution of valves in the great saphenous vein; its clinical implications, Shinohara H, Morisawa S, Toshima M, Mizukami S, *Okajiimas Folia Ant Jpn*, Oct. 1990 (Abstract).

Sapheno–femoral Valves. Histopathological Observations and Diagnostic Approach before Surgery, Leonardo Corcos, MD, Tiziana Procacci, MD, Giampiero Peruzzi, MD, Mario Dini, MD, Dinno De Anna, MD, *Dermatol Surgery*, 1996.

Repair and replacement of deep vain valves in the treatment of venous insufficiency, Wilson NM, Rutt DL, Browse NL, *Br J Surg*, Apr. 1991 (Abstract).

Experimental Prosthetic Vein Valve. Long–Term Results, Syde A. Taheri, M.D., F.A.C.A., Raymond O. Schultz, M.D., *Angiology*, vol. 46, No. 4, Apr. 1995.

External valvuloplasty of the aspheno–femoral junction, Corcos L, Peruzzi GP, Romero V, Procacci T, Zamboni P, Dini S, *Phlebologie*, Apr.–Jun. 1991. (French document).

Durability of venous valve reconstruction techniques for "primary" and postthrombotic reflux, Raju S, Fredericks RK, Neglen PN, Bass JD, *J Vasc Surg*, Feb. 1996 (Abstract).

Technical Options in Venous Valve Reconstruction, Seshadri Raju, MD, James D. Hardy, MD, *The American Journal of Surgery*, vol. 173, Apr. 1997.

Reparative surgery of valves in the treatment of superficial venous insufficiency. Exetrnal banding valvuloplasty versus high ligation or disconnection. A prospective multicentric trial, L. Corcos, D. De Anna, P. Zamboni, V. Gasbarro, V. Bresadola, T. Procacci, A. Liboni, C. Macchi, I. Donini, *Journal des Maladies Vasculaires,* 1997.

Clinical results of deep venous valvular repair for chronic venous insufficiency, William G. Jamieson, MD, FRCS, Barbara Chinnick, RN, *Can J. Surg.* vol. 40, No. 4, Aug. 1997.

Tube Collapse and Valve Closure in Ambulatory Venous Pressure Regulation; Studies With a Mechanical Model, Seshadri Ruju, MD, Austin B. Green, MS, Ruth K. Fredericks, MD, Peter N. Neglen, MD, PhD., C. Alexander Hudson, MD, Keith Koenig, PhD, *J. Endovasc Surg.* Feb. 1998.

Clinical Dynamics of Varicose Disease in Patients with High Degree of Venous Reflux During Conservative Treatment and After Surgery: 7–Year Follow–Up., Fedor Lurie, MD, PhD, Nina P. Makarova, MD PhD, *International Journal of Angiology,* May 1998.

Status of Vein Valve Transplant After 12 Months, Syde A. Taheri, MD: Louis Lazar, MD; Steven Elias, MD, *Arch Surg*—vol. 117, Oct. 1982.

Axial transformation of the profunda femoris vein, Seshadri Raju, MD; Todd Fountain, BS; Peter Neglen, MD; M. Devidas, PhD, *Journal of Vascular Surgery,* Apr. 1998, vol. 27, No. 4.

Duplex Sonographic Evaluation of the Sapheno–femoral Venous Junction in Patients with Recurrent Varicose Veins after Surgical Treatment, Joseph Elias Benabou, MD, Laszlo J. Molnar, MD, Giovanni G. Cerri, PhD, *Journal of Clinical Ultrasound;* vol. 26, No. 8, Oct. 1988.

Early experimental experience with a surgically created, totally autogenous venous valve; A preliminary report; Mark S. Rosenbloom, M.D., James J. Schuler, M.D., Rashad A. Bishara, M.D., Salve G. Ronan, M.D., and D. Preston Flanigan, M.D., *Journal of Vascular Surgery,* vol. 7, No. 5, May 1988.

Femoral vein valvuloplasty; Intraoperative angioscopic evaluation and hemodynamics improvement; Harold J. Welch, MD, Robert L. McLaughlin, RVT, and Thomas F. O'Donnell, Jr., MD, *Journal of Vascular Surgery,* vol. 16, No. 5, Nov. 1992.

In situ venous valve construction, N.M. Wilson, D.L. Rutt; N.L. Browse, *Br. J. Surg.* 1991, vol. 78, May, 595–600.

Late results after venous valve repair, I Eriksson, B. Almgren, L. Nordgren, *Inter. Angio.*, 4, 1985.

Surgical treatment of post–phlebitic syndrome, S.A. Taheri, L. Lazar and S.M. Elias, *Br. J. Surg.* vol. 69 (Suppl.) (1982) S59–S62.

Neuromyopathy in Venous Insufficiency, Syde A. Taheri, M.D., F.I.C.A., Angiology—*The Journal of Vascular Diseases,* Feb. 1988.

Vein Valve Transplantation, Syde A. Taheri, MD, David R. Pendergast, EdD, Ellot Lazar, MD, Larry H. Pollack, MD, Michael A. Meenaghan, DDS, PhD., Ronert M. Shores, AAS, Thomas Budd, PhD, Paul Taheri, BS, *The American Journal of Surgery,* vol. 150, Aug. 1985.

Technical Options in Venous Valve Reconstruction, Seshadri Raju, MD, James D. Hardy, MD., *The American Journal of Surgery,* vol. 173, Apr. 1997.

Vein valve transplant, Syde A. Taqheri, M.D., F.A.C.S., Louis Lazar, M.D., Steven M. Elias, M.D., Paul Marchard, M.D., *Surgery,* vol. 91, No. 1, Jan. 1982.

Vein valve transplant. Indiction and results, Syde A. Taheri, M.D., Reid Heffner, M.D., Michael A. Meenaghan, D.D.S., Thomas Budd, PhD., Larry H. Pollack, M.D., *Int. Angio.*, 4, 1985.

Experimental prosthetic vein valve, Syde A. Taheri, MD, David Rigan, MD, Robert Mentzer, MD, Robert M. Shores, *American Journal of Surgery,* vol. 156, Aug. 1988.

\* cited by examiner

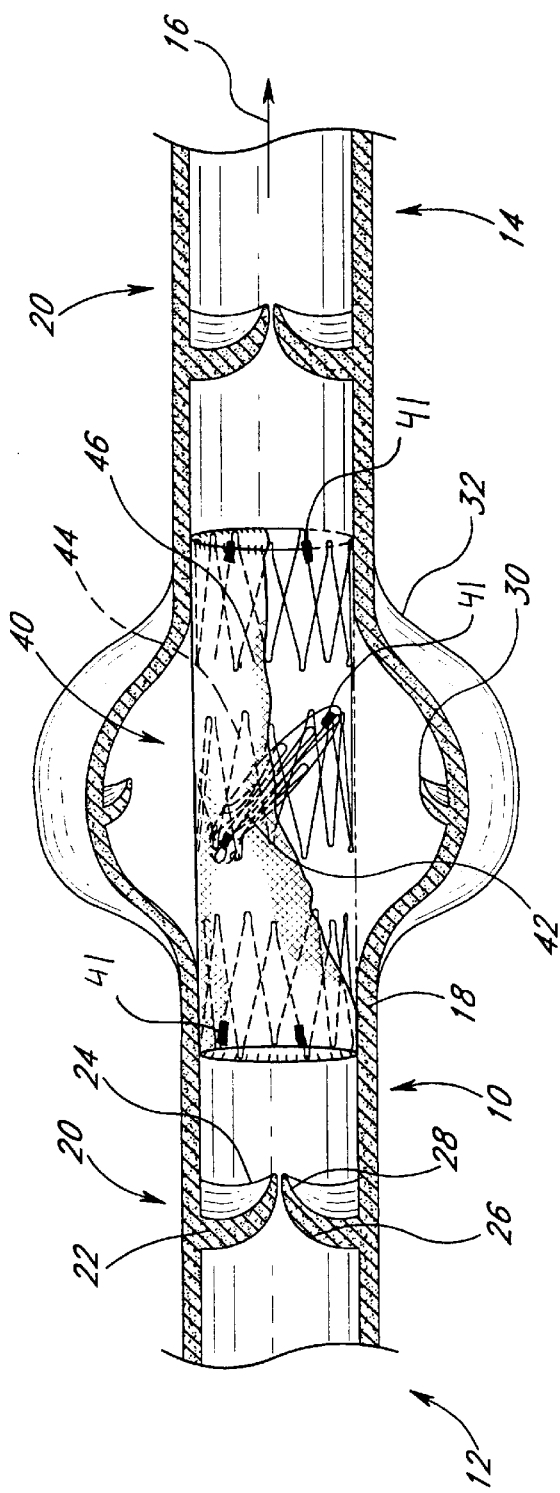
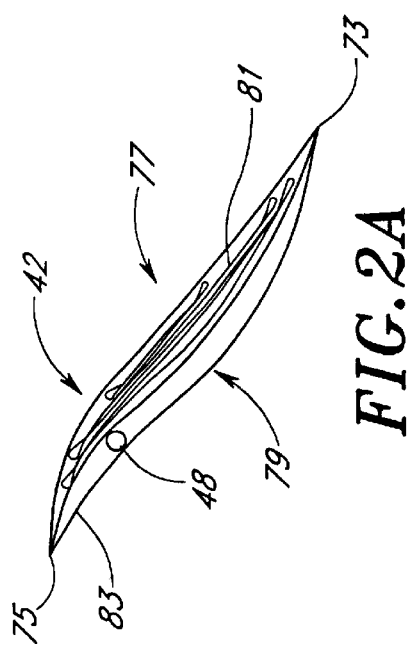
FIG. 1
FIG. 2A

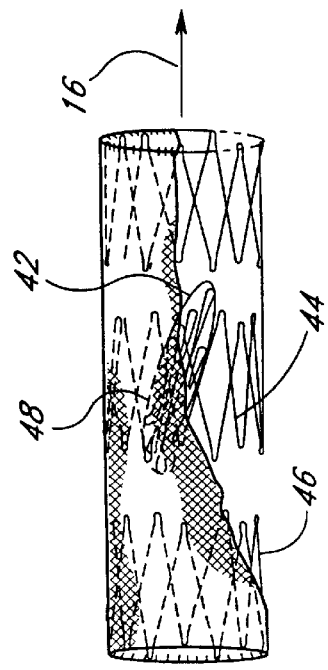
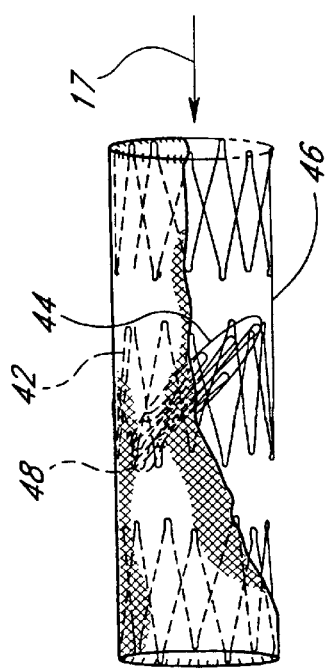
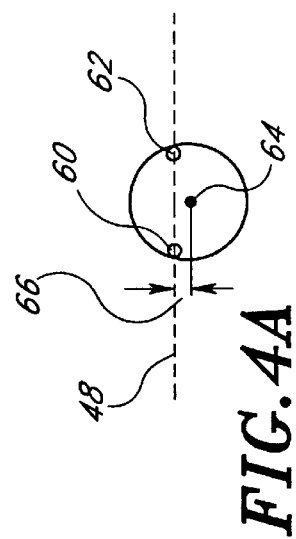
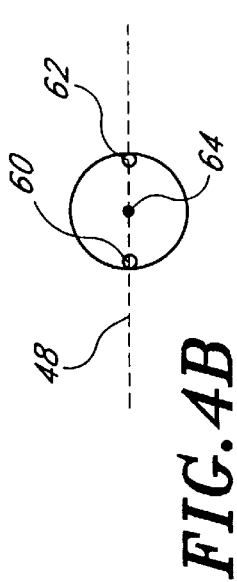
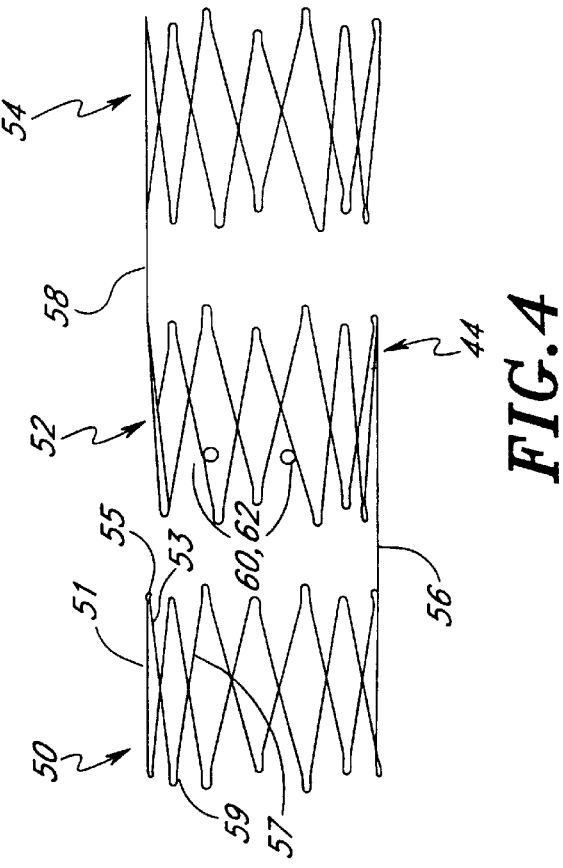

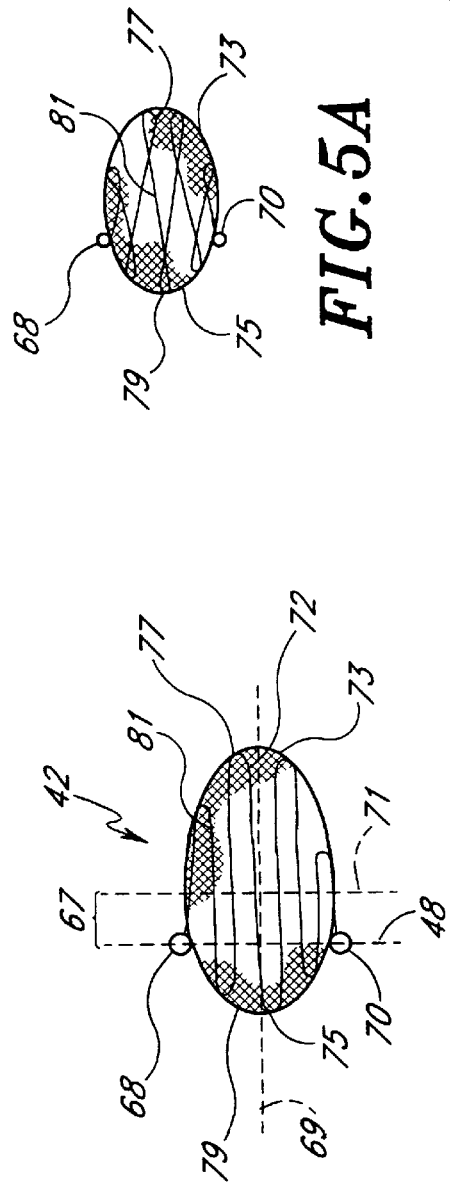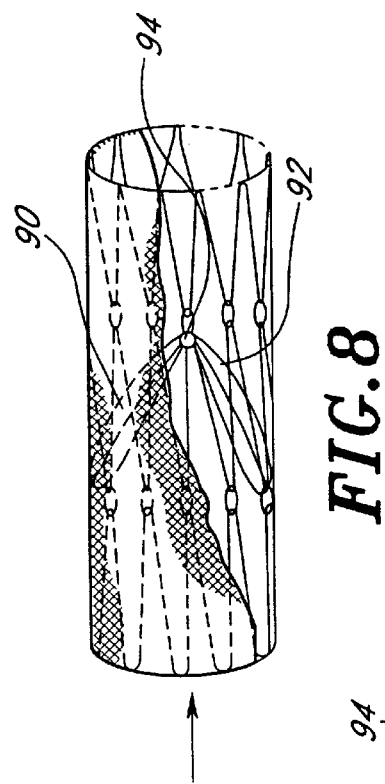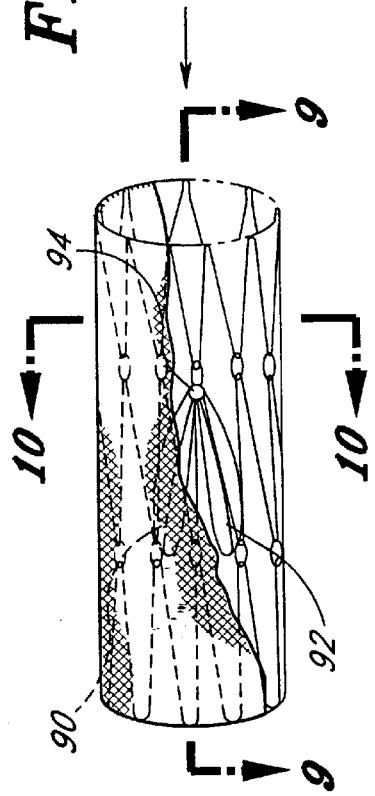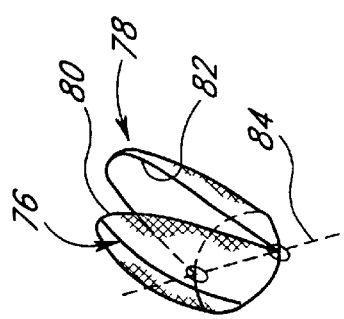

TRANSLUMINALLY IMPLANTABLE VENOUS VALVE

BACKGROUND OF THE INVENTION

Field of the Invention

This invention relates to the replacement of incompetent venous valves, and, more particularly, to minimally invasive methods and devices for transluminally implanting prosthetic venous valves.

The human venous system of the lower limbs includes the superficial venous system and the deep venous system with perforating veins connecting the two systems. The superficial system includes the great saphenous vein and the small saphenous vein. The deep venous system includes the anterior and posterior tribial veins which unite to form the popliteal vein which in turn becomes the femoral vein when joined by the small saphenous vein. The venous systems contain a plurality of valves for directing blood flow (generally superiorly) to the heart.

Venous valves are usually bicuspid valves, with each cusp forming a sack or reservoir for blood which, under pressure, forces the free edges of the cusps together to prevent retrograde flow of the blood and allow only antegrade flow to the heart. When an incompetent valve attempts to close in response to a pressure gradient across the valve, the cusps do not seal properly and retrograde flow of blood occurs.

There are two chronic venous diseases in which incompetence of venous valves is thought to be an important factor in the pathophysiology. These are chronic venous insufficiency and varicose veins.

Chronic venous insufficiency is essentially caused by venous hypertension and chronic venous stasis due to valvular incompetence both of a primitive nature (or primary or essential or idiopathic) and of a secondary nature following past illnesses of the venous system (generally speaking, deep venous thrombosis or phlebitis).

As the veins dilate due to increased pressure, the valves in the veins become less able to withstand the weight of the blood above them. This causes the veins to dilate further and the valves in the veins to fail. As they fail, the effective height of the column of blood above the feet and ankles grows taller, with an increase in the pressure exerted on the tissues of the ankle and foot. When the weight of that column reaches a critical point because of enough dilation and valve failures, the patient begins to have ulceration of the ankle which start deep and eventually come to the surface. These ulcerations are very difficult to heal because the weight of blood causing them still exists, with the tendency to enlarge the ulcer, and because they are deep, often to the bone. Chronic venous insufficiency thus consists of hypertension of the lower limb in the deep, perforating and often superficial veins with associated pigmentation, pain, swelling and ulceration.

Existing treatments for chronic venous insufficiency are less than ideal. The only therapies currently available include elevation of the legs for twenty minutes every two hours, elastic support hose to compress the veins externally and surgical repair or replacement of the valves by grafting veins from the patient's arm into the leg. These methods are variably effective. Moreover, surgery has associated complications with morbidity and mortality risk and is usually very expensive. Similarly, the palliative therapies require major lifestyle changes for the patient with potentially suboptimal long term patient compliance. Also, without repairing the valves, even if the ulcers are healed, the ulcers will recur unless the patient continues to elevate the legs and to use support hose continuously.

The varicose vein condition consists of dilatation and tortuosity of the superficial veins of the lower limb and resulting cosmetic impairment, pain and ulceration. Primary varicose veins are the result of primary incompetence of the venous valves of the superficial venous system. Secondary varicose veins occur as the result of deep venous hypertension which has damaged the valves of the perforating veins, as well as the deep venous valves.

The initial defect in primary varicose veins often involves localized incompetence of a venous valve thus allowing reflux of blood from the deep venous system to the superficial venous system. This incompetence is traditionally thought to arise at the saphenofemoral junction but may also start at the perforators. Thus, gross saphenofemoral valvular dysfunction may be present in even mild varicose veins with competent distal veins. Even in the presence of incompetent perforation, occlusion of the saphenofemoral junction usually normalizes venous pressure.

The initial defect in secondary varicose veins is often incompetence of a venous valve secondary to hypertension in the deep venous system. Since this increased pressure is manifested in the deep and perforating veins, correction of one site of incompetence could clearly be insufficient as other sites of incompetence will be prone to develop. However, repair of the deep vein valves would correct the deep venous hypertension and could potentially correct the secondary valve failure. Apart from the initial defect, the pathophysiology is similar to that of varicose veins.

Effective treatment of venous valvular incompetence remains elusive. Some methods of valvular reconstructive surgery may allow the recovery of valvular function in certain cases. However, the use of reconstructive surgery is limited by the delicate nature, and, in many cases, the irreversible damage of the valvular structure.

While bioprosthetic heart valves are known, bioprosthetic venous valves are not readily available. The major deterrent in constructing venous valves is the need to provide a valve which remains normally open, but closes under slight backflow. Another deterrent in constructing such valves is the need to provide proper valve leaflet and sinus geometry as the valve opens and closes. Prosthetic heart valves, and the current methods of preparing them, are generally not suitable as venous valve replacements. Prosthetic heart valves are usually made from porcine valves, which have a geometry unsuitable as a replacement for venous valves. These types of valves are also generally larger than venous valves, and include valve leaflets generally thicker and stiffer than the leaflets of venous valves. The thicker heart valve leaflets require a greater opening pressure, which can enhance the likelihood of venous stasis and thrombus formation, and makes such valves unsuitable for the venous system.

Thus, there remains a need for an implantable valve and related support structure and deployment system for replacing incompetent venous valves. Preferably the prosthetic valve is transluminally implantable, minimally thrombogenic, and meets the flow requirements unique to the venous system.

SUMMARY OF THE INVENTION

There is provided in accordance with one aspect of the present invention, a method of implanting a prosthetic vascular valve. The method comprises the steps of providing a prosthetic vascular valve having at least one leaflet therein. The leaflet has a minor axis extending substantially perpendicular to a longitudinal axis of the vessel, and a major axis extending perpendicular to the minor axis. The leaflet is compressed along its minor axis, to a reduced cross sectional profile and positioned within the vessel. The leaflet is thereafter permitted to self expand along its minor axis, within the vessel. Preferably, the leaflet is pivotably attached to a self expandable tubular support structure, for retaining the leaflet in a pivotable orientation within the vessel.

In accordance with another aspect of the present invention, there is provided a self expandable prosthetic venous valve. The valve comprises a tubular wire support, expandable from a first, reduced diameter to second, enlarged diameter. The tubular wire support has a flow path extending therethrough, for permitting venous blood flow.

At least on leaflet is pivotably positioned in the flow path, for permitting flow in a forward direction and resisting flow in a reverse direction. The leaflet comprises a major axis which is perpendicular to and longer than a minor axis, and the leaflet is compressible and expandable along its minor axis between a first, reduced dimension and second, enlarged dimension.

Preferably, the leaflet comprises a wire frame in which at least two longitudinal struts extend generally along the direction of the major axis and are connected by a bend. The leaflet preferably comprises at least three or four struts extending generally along the direction of the major axis.

The wire frame of the leaflet is provided with at least one and preferably two or more pivots which define an axis of rotation. Each pivot is connected to the tubular wire support, to permit the leaflet to pivot with minimal resistance between an open and closed orientation. The wire frame of the leaflet preferably further comprises a cover such as a PTFE or Dacron envelope or layer. The cover may be tied to the frame such as by 6.0 Polypropylene (Prolene™) suture.

In accordance with a further aspect of the present invention, there is provided an implantable vascular valve. The vascular valve comprises a tubular wire frame, having a proximal end, a distal end, and a flow path extending therethrough. At least one valve leaflet is moveably positioned within the flow path, and rotatable about an axis which is approximately perpendicular to the flow path. The leaflet is moveable between a closed position which is inclined within the range of from about 15° to about 75° from the axis of the flow path, and an open position which is closer to parallel with the axis of the flow path than the closed position.

Preferably, the leaflet comprises a major axis and a minor axis, and is compressible along its minor axis to a reduced, implantation cross section and self expandable along its minor axis to an enlarged, implanted cross section.

Further features and advantages of the present invention will become apparent to those of skill in the art in view of the detailed description of preferred embodiments which follows, when considered together with the attached drawings and claims.

BRIEF DESCRIPTION OF THE DRAWINGS

FIG. 1 is a schematic side elevational cross-section of a segment of a vein, illustrating a prosthetic venous valve bypassing an incompetent native valve.

FIG. 2 is an enlargement of the prosthetic valve of FIG. 1, shown in a closed orientation.

FIG. 3 is an enlargement as in FIG. 2, with the valve in an open orientation.

FIG. 4 is a schematic layout of a wire frame for supporting the prosthetic valve shown in FIG. 1.

FIG. 4a is a schematic cross-sectional view through a tubular valve support of the type illustrated in FIG. 1 showing the axis of rotation for the valve leaflet in relation to the longitudinal axis of the tubular support.

FIG. 4b is a schematic cross-sectional view as in FIG. 4a showing the axis of rotation of an alternate valve embodiment such as the two leaflet embodiment of FIGS. 7 and 8.

FIG. 5 is a schematic plan view of a laterally compressible leaflet in accordance with the present invention.

FIG. 5a is a schematic plan view as in FIG. 5, with eyes or loops at each bend.

FIG. 6 is a perspective view of a two leaflet "duck bill" valve embodiment in accordance with the present invention.

FIG. 7 is a side elevational schematic view of an alternate dual leaflet embodiment in accordance with the present invention.

FIG. 8 is a side elevational view as in FIG. 7, with the valve in the closed orientation.

DETAILED DESCRIPTION OF THE PREFERRED EMBODIMENT

Figure 10:
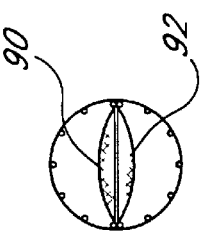
FIG. 10 is a cross-sectional view taken along the lines 10—10 in FIG. 7.

Referring to FIG. 1, there is illustrated a side elevational schematic view of a portion of a vein, including a plurality of venous valves. Although the present invention will be discussed primarily in the context of treating a patient with one or more incompetent venous valves, such as in the deep veins of the leg, the valve and valve support of the present invention may be utilized elsewhere in the body as will be appreciated by those of skill in the art in view of the disclosure herein.

Referring to FIG. 1, the vessel 10 such as a vein has an anatomically distal (inferior) portion 12, and an anatomically proximal (superior) portion 14. Normal venous blood flow 16 is from the distal 12 to the proximal 14 direction towards the heart.

The vessel 10 comprises a wall 18 and a plurality of naturally occurring valves 20. Valves 20 assist in permitting blood flow 16 in the direction of the heart and resisting reverse flow as is understood in the art. Each native valve 20 comprises a first leaflet 22 having a first edge 24 and a second leaflet 26 having a second edge 28. Leaflet edges 24 and 28 are coaptive in a normally functioning valve, to permit forward and inhibit reverse blood flow.

Due to any of a variety of underlying etiology, as discussed in part in the background of the invention, one or more valves 30 may become incompetent. As used herein, an incompetent valve is a valve which fails to adequately resist reverse blood flow. In the illustrated embodiment, incompetent valve 30 is associated with a portion of the vessel wall 32 which has become diseased or otherwise weakened so that the opposing leaflets of incompetent valve 30 are no longer able to coaptively close and inhibit retrograde blood flow.

A self expandable prosthetic venous valve graft 40 is illustrated spanning the diseased or weakened wall section 32. Venous valve graft 40 includes one or more valve leaflets 42 pivotably or moveably supported within a frame 44. As used herein, "leaflet" refers to a component of the valve which is moveable between a first position in which blood is permitted to flow in a forward direction, and a second position which inhibits blood flow in a reverse direction. Frame 44 in the illustrated embodiment is provided with a tubular cover 46 such as a flexible, thin walled PTFE or Dacron sleeve.

The length and diameter of the overall venous valve graft 40 can be varied widely, depending upon the intended clinical application. In the context of a venous valve support intended to span an incompetent venous valve 30 in the deep veins of the leg in an adult, venous valve graft 40 will typically have an axial length within the range of from about 2 to about 20 centimeters, and often between about 6 and 14 centimeters. In one embodiment, the venous valve graft 40 has an axial length of about 10 centimeters. In general, the length of the venous valve graft 40 is preferably sufficient to fully span the axial length of the diseased or weakened wall section 32, and overlap with proximally and distally adjacent healthy tissue by a sufficient distance (e.g., 1–4 cm) to firmly position the venous valve graft 40 in the vein with minimal or no risk of migration. Thus, venous valve graft 40 may be constructed having differing lengths depending upon the size of the diseased or weakened wall portion 32 or other treatment site, such as a treatment site which spans two or three or more venous valves 20 which have become diseased and are desirably spanned.

In the case of a patient having multiple incompetent venous valves 30, a single relatively long venous valve graft 40 can be provided having one or more prosthetic valves positioned therein to span two or three or more native valves. Alternatively, as a matter of clinical judgment, a physician may prefer to install two or three or more discrete venous valve grafts 40 positioned axially apart along the length of the vein.

In general, the venous valve graft 40 of the present invention is collapsible into a first, reduced cross-sectional configuration such as for transluminal implantation into the treatment site, and subsequently radially enlargeable to a second, larger diameter for retention and functioning within the vein. In the preferred embodiment, the venous valve graft 40 is biased into the second, larger diameter. In this manner, implantation of the valve graft 40 can be accomplished by restraining the valve graft in the first, reduced cross sectional configuration as will be discussed and implanting the valve graft 40 by releasing it from the retention catheter. The valve graft 40 will thereafter radially expand within the treatment site to the extent necessary to fit the vessel. A radially outwardly biased valve graft 40 further assists in responding to compression pressures which may be experienced as a result of external compression on the leg, bending of the knee or other anatomical movement which places a momentary compressive force on the valve graft 40.

The expanded diameter of the venous valve graft 40 can be varied depending upon the intended use, as will be apparent to those of skill in the art. The second enlarged diameter for a typical deep vein in the leg is on the order of from about 8 mm to about 14 mm, although other dimensions may be utilized as may be desired. Preferably, a venous valve graft 40 will be selected for a particular vein, having a greater unconstrained expanded diameter than the inside diameter of the adjacent healthy portions of the vessel 10. In this manner, the proximal and distal end attachment zones on the valve graft 40 will exert a radially outwardly directed force on the vessel wall to assist in retention of the valve graft 40.

Preferably, two or more radiopaque markers 41 are provided for enabling visualization of the graft during deployment, as well as to enable post deployment evaluation of the position of the graft. Preferably, one or two or more radiopaque markers are provided on the proximal end of the graft and one or more markers are provided on the distal end of the graft. In addition, at least one and preferably two radiopaque markers are provided on the valve leaflet. This will enable evaluation of the operation of the leaflet following implantation. The radiopaque markers may comprise gold, platinum, or other materials which are known in the art.

Referring to FIG. 2, there is illustrated an enlarged fractional view of the valve of FIG. 1, with the valve leaflet 42 illustrated in a closed orientation. In the illustrated embodiment, the valve leaflet pivots about a rotational axis 48, which is displaced laterally from the longitudinal axis 64 of the vessel and of the venous valve graft 40 by an offset distance 66 as illustrated in FIG. 4a. Offset distance 66 cooperates with the generally elliptical profile and closure angle of the leaflet 42, discussed below, to allow blood flow in the reverse direction to pivot the leaflet 42 into a closed orientation as seen in FIG. 2. Alternatively, blood flow in a forward direction 16 (FIG. 3) creates a greater net forward force moment on the leaflet 42 on the leaflet side of the rotational axis 48 so that the leaflet 42 opens to permit forward flow. In this manner, the valve can pivot between an open and closed orientation under very low fluid force, which is an important characteristic in the context of venous valves.

The outer tubular cover 46 may be provided with radial support throughout its axial length, or, as in the illustrated embodiment, periodic radial support. Referring to FIG. 4, there is illustrated a wire layout which may be utilized to construct the wire frame 44 of the venous valve graft 40 illustrated in FIG. 1. Any of a wide variety of wire configurations can be utilized in the context of the present invention, as will be appreciated by those of skill in the art in view of the disclosure herein. For example, self-expandable wire structures useful for creating self expandable wire frames capable of supporting one or more valve leaflets 42 are disclosed in U.S. Pat. No. 5,800,508 issued Sep. 1, 1998 to Goicoechea et al., entitled Bifurcated Endoluminal Prosthesis; U.S. Pat. No. 5,665,115 issued Sep. 9, 1997 to Cragg entitled Intraluminal Stent; and U.S. Pat. No. 5,507,767 issued Apr. 16, 1996 to Maeda et al. entitled Spiral Stent, the disclosures of which are incorporated in their entireties herein by reference.

Wire frame 44 comprises at least a first zigzag section of wire 50, and may additionally comprise a second zigzag section of wire 52 and a third or more zigzag section of wire 54. Each zigzag section of wire 50 comprises at least two and preferably from about 4 to about 10 substantially straight segments 51, 53, joined together by, for example, a proximal bend 55. Segment 53 is connected to a segment 57 by a distal bend 59. Each zigzag section of wire 50 preferably comprises at least about 3 or 4 and as many as 6 or 7 or 8 or more proximal bends 55 and corresponding distal bends 59.

Each of the sections 50 and 52 are connected by at least one connector 56, and each of the sections 52 and 54 are connected by at least one connector 58. In the illustrated embodiment, the overall wire layout is constructed from a single length of wire. Each of the zigzag sections 50, 52 and 54 may be formed on a cylindrical mandrel, or formed flat and rolled about a longitudinal axis and secured such as by soldering or suture into a tubular configuration which is utilized to support the cover 46. This construction conveniently allows radial compression such as for loading within a low profile deployment catheter and self-expansion within the treatment site as will be understood by those of skill in the art.

Where relatively greater radial strength is desired, two or more adjacent zigzag sections 50, 52 can be placed immediately adjacent each other with one or more apexes (e.g., 55, 59) of opposing zigzag sections connected as is illustrated, for example, in FIGS. 4A through 4F and associated disclosure in U.S. Pat. No. 5,800,508, and FIGS. 2 through 4 in U.S. Pat. No. 5,665,115 the disclosures of which have been incorporated herein. Wire or suture loops may be used to connect opposing bends on adjacent sections of a multi-section graft. Alternatively, single section grafts may be used where an overall length for the valve graft is less than about 4 cm and particularly less than about 2 cm or 3 cm.

The wire frame 44 is preferably provided with two or more hinge loops 60 and 62 for pivotably supporting one or more valve leaflets 42. In the illustrated embodiment, hinge loops 60 and 62 are aligned on and provide a rotational axis 48 for a single leaflet valve as illustrated in FIGS. 1–3. The rotational axis 48 is located with an offset distance 66 from the longitudinal axis 64 as is illustrated in FIG. 4a. Offset distance 66 is preferably at least about 2 mm and generally within the range of from about 10 to about 30 percent of the expanded diameter of the venous valve graft 40.

Referring to FIG. 5, there is illustrated a schematic view of the leaflet 42 for use in the embodiment illustrated in FIGS. 1–3. Leaflet 42 has a generally elliptical profile, having a major axis 69 and a minor axis 71. The generally elliptical profile of the leaflet 42 enables the leaflet to close a tubular structure such as venous valve graft 40 while oriented at an angle of between 0° and 90° with respect to the longitudinal axis of the venous valve graft 40 as may be seen in FIGS. 1 and 2. The closure angle of the leaflet 42 may be adjusted by optimizing the offset distance 66 and the length of the major axis 69 to adjust the opening flow volume and closing flow volume necessary to operate the valve as will be appreciated by those of skill in the art.

In a single leaflet embodiment, the leaflet 42 is preferably moveable between an open position in which the plane which best fits the leaflet is substantially parallel with the axis of blood flow (FIG. 3) and a closed position in which the plane which best fits the leaflet is inclined with respect to the axis of blood flow (FIG. 2). Generally, the leaflet in the closed position is inclined within the range of from about 15° to about 75° from the axis of the flow path, and preferably, within the range of from about 30° to about 60° from the axis of the flow path. In multiple leaflet embodiments, closure angles within approximately the same ranges are presently contemplated.

The leaflet frame 72 preferably comprises a bendable wire which has been formed into a series of zigzag bends as illustrated in FIG. 5. As illustrated therein, the leaflet frame 72 comprises a plurality of bends 77 on a leading edge 73 of the leaflet 42. A plurality of trailing edge bends 79 are provided on a trailing edge 75 of the leaflet 42. In the illustrated embodiment, four leading edge bends 77 are connected to three trailing edge bends 79 by a plurality of struts 81. Anywhere within the range of from about 2 to 8 leading edge bends 77 may be connected with anywhere in the range of from about 2 to 8 trailing edge bends 79 in the presently contemplated embodiment. Additional leading edge bends 77 and trailing edge bends 79 together with corresponding struts 81 may be provided as desired. However, excessive struts 81 and corresponding bends will negatively impact the crossing profile of the collapsed leaflet 42 as will be apparent in view of the disclosure herein.

Preferably, in the fully expanded leaflet 42, the struts 81 will extend substantially parallel to the major axis 69 of the leaflet 42. The deviation of any given strut 81 from parallel to the major axis 69 in the expanded leaflet 42 will be a function of the number of leading edge bends 77 and trailing edge bends 79 as will be apparent in view of the disclosure herein. This construction permits the leaflet 42 to be compressed laterally along its minor axis 71 such as for loading into the deployment catheter, and transluminally positioning with the vessel. Leaflet 42 is collapsed within the wire frame 44 throughout the deployment process. Following deployment from the delivery catheter, both the frame 44 and one or more leaflets 42 positioned therein will self expand to the implanted, functional dimension.

Preferably, the minor axis dimension of the leaflet 42 is compressible to no more than about 1.0 mm and preferably no more than about 0.5 mm in a leaflet 42 having an implanted minor axis 71 dimension of about 8–12 mm.

The leaflet frame 72 is thereafter provided with a flexible leaflet cover 74 such as a layer of PTFE or Dacron secured to one or both sides of the leaflet frame 72 or an envelope for surrounding the frame 72. In one embodiment, the leaflet frame 72 is surrounded on both sides by a leaflet cover 74 in the form of a pocket of PTFE. The PTFE pocket surrounds both sides and the edges of the leaflet 42, and functions in part to obstruct blood flow through the struts 81 as well as to limit the minor axis 71 expansion of the leaflet 42 at the desired dimension. Any of a wide variety of materials may be utilized as the web or coating on struts 81, and still accomplish the blood flow blocking function of the leaflet 42.

Preferably, the leaflet material will be a polymeric or thin film metal material which exhibits minimal thrombogenic activity. Alternatively, the material of the leaflet cover 74 may be provided with any of a variety of nonthombogenic coatings as are understood in the coronary stent and other implantable cardiovascular device arts. In general, both the leaflet and the other portions of the graft are provided with anti-thrombogenic surfaces or surface treatments to minimize thrombosis formation over the leaflet and throughout the graft. Although the present inventors do not presently contemplate a preferred anti-thrombogenic surface treatment, a variety are known in the implantable prosthetic device arts. Such coatings for treatment include chemical treatment, Corona surface treatments, treatments to reduce the surface energy to reduce thrombosis formation, and materials which are inherently anti-thrombogenic.

The leaflet 42 is provided with a first connector 68 and a second connector 70, for pivotable connection to the first hinge loop 60 and a second hinge loop 62 on frame 44. See FIG. 4. Preferably, first connector 68 and second connector 70 are loops on the leaflet frame 72 which can be looped within the hinge loops 60 and 62 to provide a very low friction pivotable connection. This construction enables the prosthetic venous valve to have a relatively high reverse "break" pressure and a very low forward opening pressure.

The first connector 68 and second connector 70 are preferably located on a rotational axis 48 which, in the illustrated embodiment, is parallel to the minor axis 71 of the valve leaflet 42 but offset by a distance 67 which corresponds to the offset distance 66 illustrated in FIG. 4a. Preferably, pivoting of the valve leaflet 42 is further enhanced by forming the leaflet 42 in a slightly nonplanar orientation as illustrated in FIG. 2a. As illustrated therein, and previously discussed, the rotational axis 48 is offset from the minor axis 71 so that it is nearer to a trailing edge 75 than a leading edge 73. Valve closure may be facilitated by providing a proximal concavity 81 on a proximal face 77 of the valve leaflet 42 in between the rotational axis 48 and the leading edge 73. A distal concavity 83 may be provided on a distal face 79 of leaflet 42, in between the rotational axis 48 and trailing edge 75. This contouring of the leaflet 42 may facilitate opening and closing of the valve as well as allow the proximal face 77 to be optimized for closing under minimal retrograde flow.

In this embodiment, closing efficiency of the valve is a function of the difference in the surface area on proximal face 77 between rotational axis 48 and leading edge 73 and the surface area of distal face 79 between rotational axis 48 and trailing edge 75. In general, closing force on the leaflet 42 will increase as the rotational axis 48 is positioned closer to trailing edge 75. Thus, leaflet 42 may be pivotably attached to the side wall of the frame 44 at its trailing edge 75. However, rotational axis 48 is preferably spaced apart from the trailing edge 75 by a sufficient distance to allow blood flow on both surfaces of the leaflet 42 when opened, to minimize stasis and potential thrombus formation. Optimization of the location of rotational axis 48 in combination with the contouring of distal concavity 83 and proximal concavity 81, if present, can be accomplished through routine experimentation by one of skill in the art in view of the disclosure herein.

Two coaptive leaflets may be constructed in accordance with the foregoing principles, in which two leading edges 73 provide a coaptive closure against each other. In this embodiment, a first leaflet 42 is provided with a first rotational axis 48. A second leaflet 42 is positioned symmetrically across the longitudinal axis of the vessel from the first leaflet 42, and has a coaptive leading edge 73 and a second rotational axis 48 located in the same transverse plane perpendicular to the longitudinal axis of the flow path as the first rotational axis 48.

Referring to FIG. 6, there is illustrated one embodiment of a two leaflet "duck bill" valve in accordance with the present invention. The valve comprises a first leaflet 76 having an edge 80 thereon for cooperating with an edge 82 on second leaflet 78. The leaflets 76 and 78 comprise a plurality of flexible wire struts, covered by a blood flow blocking membrane such as PTFE or Dacron as has been discussed. Each of the leaflets 76 and 78 are rotatably connected to the inside wall of a tubular wire frame 44, such as through the use of interconnecting loops or other pivotable connection.

Preferably, the edges 80 and 82 are pivotable towards each other to close the valve and away from each other to open the valve with little or no spring bias, and in response to blood flow. The first leaflet 76 and second leaflet 78 are contoured with a medially facing concavity, so that forward blood flow from the rotational axis 84 in the direction of the first and second leaflet edges 80 and 82 will tend to open the valve, while reverse direction flow will operate on the lateral surfaces of the first and second leaflet 76 and 78 to close the valve.

The first and second leaflets 76 and 78 may be connected together at about the rotational axis 84, or may be independently pivotably connected to the interior surface of the wire frame 44. Due to the wire construction of the first and second leaflets 76 and 78, the leaflets may be radially compressed for loading within the deployment catheter, and will thereafter radially expand into a functional orientation following deployment.

Referring to FIG. 7, there is provided a side elevational view of an alternate two-leaflet embodiment of the valve. The valve comprises a first leaflet 90 and second leaflet 92 which are independently connected to and/or folded over a rotational axis 94. As illustrated in FIG. 8, reverse blood flow causes the first and second leaflets 90 and 92 to rotate radially outwardly into a closed orientation. Forward flow folds the first and second leaflets 90 and 92 into a low profile flow permitting orientation as seen in FIGS. 7 and 10.

Figure 9:
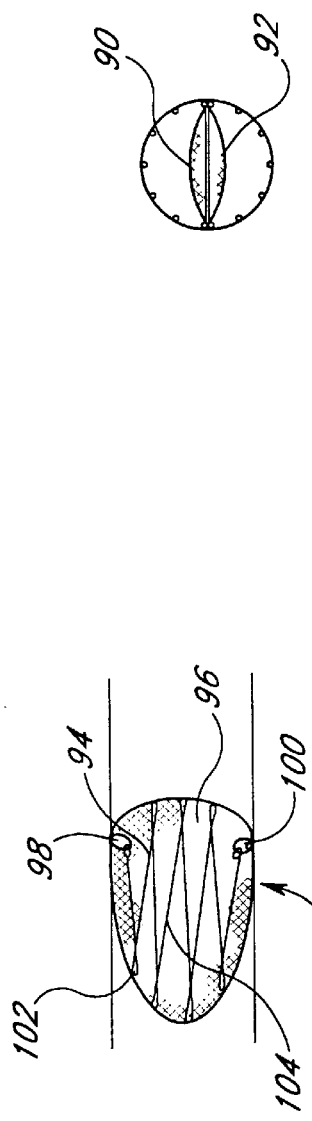
FIG. 9 is a schematic plan view of the leaflet as seen along the lines 9—9 in FIG. 7.

Referring to FIG. 9, each of the leaflets 90 and 92 is preferably formed from a self-expandable and compressible wire frame 94 which permits collapsing into a reduced cross-sectional profile for positioning within the deployment catheter, and self-expanding at the treatment site to form the leaflet 90 and 92. The frame 94 is preferably covered on one or both sides by a cover 96 such as a Dacron or PTFE sleeve as has been discussed in connection with previous embodiments. The wire frame 94 preferably comprises a plurality of straight segments 104 separated by a plurality of bends 102. Each of the bends 102 may comprise either a simple bend in the wire 94 or a loop as illustrated, such as to enhance opening force following deployment of the valve. The wire frame 94 is further provided with at least a first pivot 98 and second pivot 100, aligned along the rotational axis 94, to permit functioning of the valve as will be appreciated in view of the disclosure herein. First pivot 98 and second pivot 100 are preferably connected to corresponding connectors on the frame 44 for the prosthetic venous valve graft 40.

Figure 11:
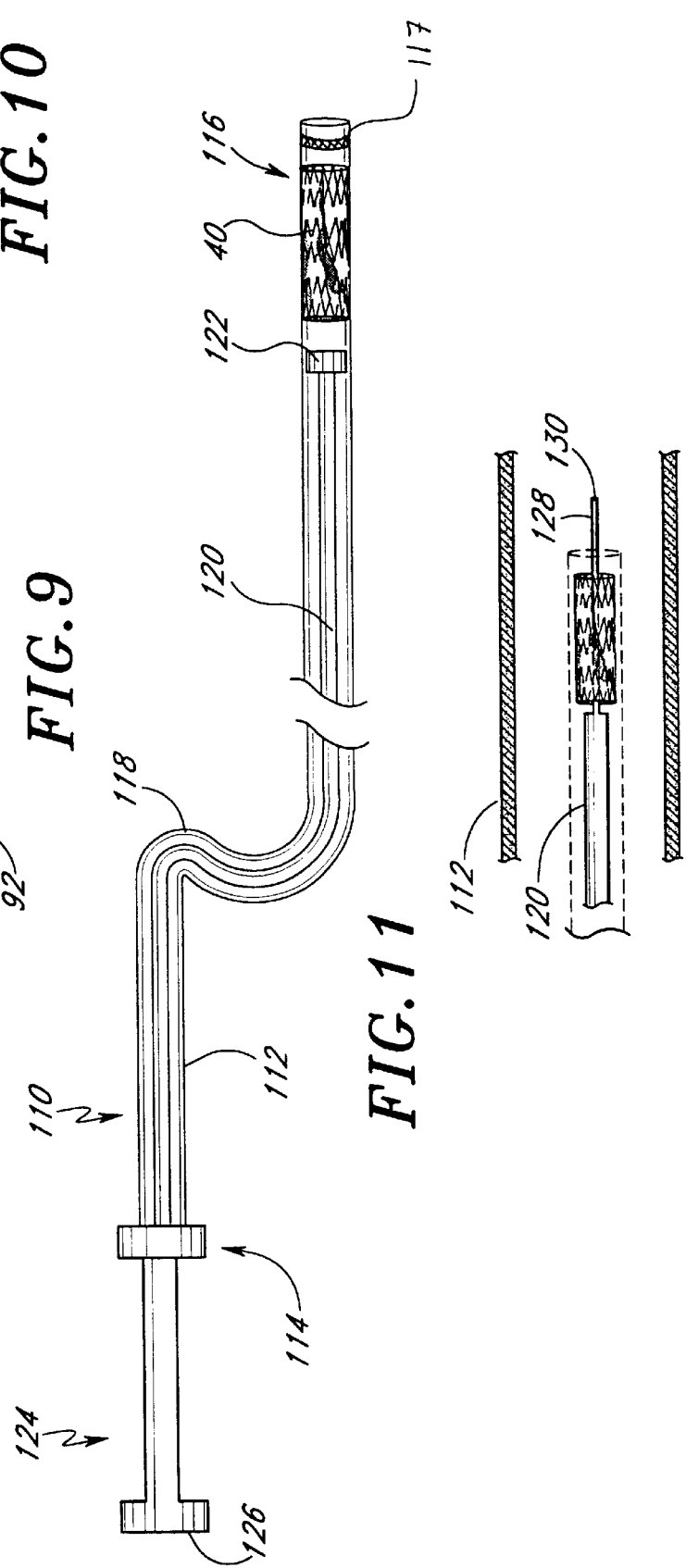
FIG. 11 is a side elevational cross-section of a deployment catheter in accordance with one aspect of the present invention.

Referring to FIG. 11, there is illustrated one embodiment of a deployment catheter 110 in accordance with the present invention. The deployment catheter 110 generally comprises an elongate flexible body 112 having a proximal end 114 and a distal end 116. At least one radiopaque marker band 117 is provided on or near distal end 116 to facilitate positioning of the catheter and as a reference to monitor the deployment status. Elongate flexible catheter body 112 has a length sufficient to reach from the percutaneous access site to the treatment site. In general, access to the venous treatment site will be accomplished through a cut down or introduction of an introducer, and catheters having a length on the order of from about 50 cm to about 70 cm are presently contemplated. However, other catheter lengths may readily be constructed to suit particular target sites and access sites.

The elongate flexible body 112 preferably has an outside diameter within the range of from about 7 French (2.3 mm) to about 10 French (3.3 mm) in an embodiment intended for implanting a prosthetic venous valve graft 40 within the deep veins of the leg. Body 112 may be constructed in any of a variety of manners well known in the catheter manufacturing arts, such as by extrusion of any of a variety of known biocompatible materials including high density polyethylene, Pebax, and PTFE or FEP.

Figure 12:
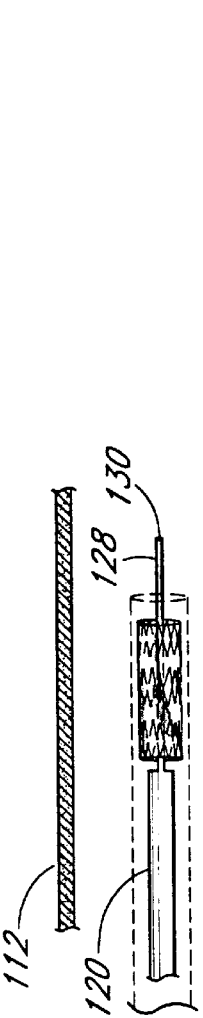
FIG. 12 is an enlarged cross-sectional view of an alternate distal end configuration for a deployment catheter in accordance with the present invention.

Catheter body 112 is provided with an elongate central lumen 118 for axially moveably receiving an elongate flexible deployment core 120. A distal portion of the flexible body 112 has an inside diameter sufficient to receive the collapsed venous valve graft 40 as illustrated in FIGS. 11 and 12. The deployment core is provided with a transverse pushing surface 122 for contacting the proximal end or other portion of the venous valve graft 40. The proximal end 124 of the deployment core 120 is provided with a control 126, so that distal advancement of the control 126 with respect to the body 112 will enable distal deployment of the venous valve graft 40 from the catheter 110. In practice, the preferred clinical deployment technique is believed to involve axial retention of the deployment core 120 while the tubular body 112 or a distal tubular sheath is proximally retracted to release the venous valve graft 40, to enhance precision during placement of the venous valve graft 40.

In an alternate embodiment of the core 120 illustrated in FIG. 12, the core 120 has a distal extension 128 which extends coaxially throughout the length of the venous valve graft 40. A guidewire lumen 130 extends axially throughout the length of the core 120 and distal extension 128, to permit navigation of the deployment catheter 112 over the wire as is well understood in the art. Additional lumen may be provided on the deployment catheter 110 as may be desired, such as for infusion of contrast media, anticoagulants, or other drugs or materials.

In accordance with the use of the present invention, one or more incompetent valves 30 are identified in a patient. A deployment catheter 110 is provided, having a radially compressed venous valve graft 40 positioned therein. The deployment catheter 110 is introduced into the vessel, and transluminally advanced until the distal end 116 is positioned at or about the (anatomically) proximal portion of the diseased or weakened wall section 32. One or more radio opaque markers may be provided on the venous valve graft 40 and/or the catheter 110 to facilitate positioning relative to the incompetent valve 30. Following confirmation of location of the deployment catheter 110, the retention sheath or catheter body 112 is proximally withdrawn while the deployment core is retained in its axial position so that the venous valve graft 40 is deployed from the distal end 116 of the catheter 110. As the venous valve graft 40 is deployed, it will self-expand within the vessel, as will be apparent to those of skill in the art in view of the disclosure herein. The deployment catheter 110 may thereafter be transluminally withdrawn from the patient. Proper functioning of the leaflet 42 or two or more leaflets in alternate embodiments may be confirmed through any of a variety of manners, such as through the infusion of radio opaque dye, or the observation of radio opaque markers positioned on the leaflet 42.

A further application for the valvular prosthesis of the invention is in the treatment of congenital defects of the right ventricular outflow tract. For example, a valvular prosthesis in the form of a tubular member bearing at least one venous valve may be used to bypass a defective semilunar valve of the pulmonary artery, or even a defective pulmonary artery. Examples of defects of the right ventricular outflow tract are truncus arterioles, pulmonary atresia and pulmonary stenosis.

Truncus arteriosus is a congenital cardiovascular malformation where a single artery, formed by the joining of the pulmonary and aortic arteries, arises from the heart. This single artery typically bridges the right and left ventricles. This congenital defect may also be accompanied by a ventricular septal defect, which is a hole through the heart wall between the right and left ventricles.

While the mortality from this defect is high, attempts are usually made to repair the defect. This involves surgically separating the pulmonary segment from the aortic segment, and sealing the resulting opening of the aortic artery. If present, the ventricular septal defect is repaired by suturing the opening closed or suturing a patch over the opening. The pulmonary artery is then reconstructed by various techniques, which usually require the construction or insertion of a valve.

One technique utilizes a homograph which is surgically interposed in a graft sutured between the right ventricle and the pulmonary artery. For a more detailed discussion of this technique, see "Truncus Arteriosus," Chapter 28 of *CARDIAC SURGERY Morphology, Diagnostic Criteria, Natural History, Techniques, Results, and Indications,* by John W. Kirklin, M. D. and Brian G. Barratt-Boyes, KBE, MB, ChM, Published by John Wiley & Sons (1986).

In accordance with another application of the present invention, the transluminally implantable venous valve graft may be useful in treating dialysis associated central venous stenosis or central venous stasis. Central venous stenosis occurs in up to 22% of patients with functioning dialysis grafts in an upper extremity. Development of such lesions limits the usefulness of that limb for dialysis purposes. Surgical access to these veins is difficult because of their location within the neck and chest. The efficacy of the current therapeutic endovascular techniques is subject to improvement. Thus, the transluminally implantable venous graft valve of the present invention may be utilized in treating central venous stenoses or central venous stasis associated with dialysis grafts.

Although the present invention has been described in terms of certain preferred embodiments, other embodiments will be apparent to those of skill in the art in view of the disclosure herein. Accordingly, the foregoing embodiments are illustrative only, and not intended to limit the scope of the invention. Instead, the scope of the invention is to be assessed only by reference to the attached claims.

What is claimed is:

1. A self expandable prosthetic venous valve, comprising:

a tubular wire support, expandable from a first, reduced diameter to a second, enlarged diameter, and having a flow path therethrough; and at least one leaflet pivotably positioned in the flow path for permitting flow in a forward direction and resisting flow in a reverse direction, the leaflet comprising an internal support having a first pivot point and a second pivot point attached to opposing sides of the tubular support, and a rotational axis extending through the first and second pivot points;

wherein the leaflet comprises a major axis which is perpendicular to and longer than a minor axis, and the leaflet is compressible and expandable along its minor axis between a first, reduced dimension and a second, enlarged dimension.

2. A self expandable valve as in claim 1, wherein the leaflet comprises a wire frame having a first eyelet and a second eyelet thereon.

3. A self expandable valve as in claim 2, wherein the wire comprises at least two longitudinal struts extending generally along the direction of the major axis and connected by a bend.

4. A self expandable valve as in claim 3, comprising at least four longitudinal struts and at least three bends.

5. A self expandable valve as in claim 3, further comprising at least two pivots on the tubular wire support defining an axis of rotation.

6. A self expandable valve as in claim 5, wherein each pivot comprises a wire loop for pivotable attachment to the leaflet.

7. A self expandable valve as in claim 2, further comprising a cover on the wire frame.

8. A self expandable valve as in claim 1, wherein the tubular support comprises a plurality of substantially straight sections separated by a plurality of bends.

9. A self expandable valve as in claim 8, further comprising a tubular polymeric sleeve on the tubular support.

10. A self expandable valve as in claim 5, wherein the axis of rotation is substantially perpendicular to the major axis.

11. An implantable vascular valve, comprising:

a tubular wire frame, having a proximal end, a distal end and a flow path extending therethrough; and at least one valve leaflet moveably positioned within the flow path, the valve leaflet rotatable about an axis which is approximately perpendicular to the flow path and spaced apart from the tubular wire frame by a sufficient distance to allow blood flow on both surfaces of the leaflet when in an open position;

wherein the leaflet is moveable between a closed position which is inclined within the range of from about 15° to about 75° from the axis of the flow path and the open position which is closer to parallel with the axis of the flow path than the closed position.

12. An implantable vascular valve as in claim 11, wherein the leaflet comprises a major axis and a minor axis, and the leaflet is compressible along its minor axis to a reduced, implantation cross section and self expandable along its minor axis to an enlarged, implanted cross section.

13. A method of implanting a prosthetic vascular valve, comprising the steps of:

providing a prosthetic vascular valve having at least one leaflet therein, said leaflet having a supporting frame, a minor axis extending substantially perpendicular to a longitudinal axis of the vessel, and a major axis extending perpendicular to the minor axis;

compressing the leaflet along its minor axis, to a reduced cross sectional profile;

positioning the leaflet in a peripheral vein; and permitting the leaflet to self expand along its minor axis within the vein.

14. A self expandable prosthetic venous valve, comprising:

a tubular wire support, expandable from a first, reduced diameter to a second, enlarged diameter, and having a flow path extending therethrough;

a first leaflet, pivotably attached to the tubular wire support, said leaflet having zig zag frame, a base at a first end and a coaptive edge at a second end;

a second leaflet pivotably attached to the tubular wire support, said second leaflet having a zig zag frame, a base and a coaptive edge end;

the first and second leaflets pivotable about first and second axes, respectively, the first and second axes extending transversely through the tubular wire support;

wherein the first and second leaflet are configured to permit blood flow in a forward direction from the base through the coaptive edges, and the coaptive edges are brought into contact with each other to obstruct the flow path in response to blood flow in a reverse direction.

15. A valve as in claim 14 wherein each of the first and second axes are spaced apart from each other.

16. A valve as in claim 14 wherein each leaflet comprises a blood flow restricting membrane thereon.

17. A self expandable prosthetic venous valve as in claim 1, wherein the leaflet is provided with an anti-thrombogenic surface.

18. An implantable vascular valve as in claim 11, wherein the leaflet is provided with a surface for minimizing thrombus formation.

* * * * *